(12) United States Patent
Malik

(10) Patent No.: US 6,897,348 B2
(45) Date of Patent: May 24, 2005

(54) BANDAGE, METHODS OF PRODUCING AND USING SAME

(75) Inventor: Sohail Malik, Roswell, GA (US)

(73) Assignee: Kimberly Clark Worldwide, Inc, Neenah, WI (US)

( * ) Notice: Subject to any disclaimer, the term of this patent is extended or adjusted under 35 U.S.C. 154(b) by 253 days.

(21) Appl. No.: 10/035,059

(22) Filed: Dec. 28, 2001

(65) Prior Publication Data

US 2003/0125654 A1 Jul. 3, 2003

Related U.S. Application Data

(63) Continuation-in-part of application No. 10/026,292, filed on Dec. 19, 2001.

(51) Int. Cl.$^7$ .......................... A61F 13/00; A61L 15/16
(52) U.S. Cl. ......................................... 602/48; 424/447
(58) Field of Search ............................. 424/447; 602/48

(56) References Cited

U.S. PATENT DOCUMENTS

| | | | |
|---|---|---|---|
| 2,040,879 A | 5/1936 | Rigby | |
| 2,040,880 A | 5/1936 | Rigby | |
| 2,510,993 A | 6/1950 | Meyer et al. | |
| 2,795,579 A | 6/1957 | Doczi | |
| 3,328,259 A | 6/1967 | Anderson | |
| 3,338,992 A | 8/1967 | Kinney | |
| 3,341,394 A | 9/1967 | Kinney | |
| 3,419,006 A | 12/1968 | King | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,976,563 A | 8/1976 | Scalco | |
| 4,100,324 A | 7/1978 | Anderson et al. | |
| 4,147,775 A | 4/1979 | Schwartz et al. | |
| 4,147,831 A | 4/1979 | Balinth | |
| 4,192,299 A | 3/1980 | Sabatano | |
| 4,340,563 A | 7/1982 | Appel et al. | |

(Continued)

FOREIGN PATENT DOCUMENTS

| | | |
|---|---|---|
| EP | 020697 A2 | 12/1986 |
| EP | 0331471 B1 | 9/1989 |
| EP | 0361722 B1 | 12/1993 |
| EP | 0601080 B1 | 6/1994 |
| EP | 1008330 A2 | 6/2000 |
| WO | 96/13282 | 5/1996 |
| WO | 97/28832 | 8/1997 |
| WO | 99/59647 | 11/1999 |
| WO | 00/12038 | 3/2000 |

OTHER PUBLICATIONS

Abstract, DE 3912122A1, Wella AG (Wela); Oct. 25, 1990.
Abstract, JP 60–219202A, Daicel Chem. Ind. Ltd., Nov. 1, 1995.

(Continued)

*Primary Examiner*—John J. Calvert
*Assistant Examiner*—Linh Truong
(74) *Attorney, Agent, or Firm*—James B. Robinson; Steven Flack

(57) ABSTRACT

An adhesive bandage of the type used on acute wounds, burn wounds, minor wounds, or irritations includes a first layer for covering the wound site and an area around the wound site. The first layer includes a top surface and bottom surface. A second adhesive layer is situated over the first layer bottom surface, for adhering the adhesive bandage to a wound site. A third absorbent layer is situated over the second layer, for absorbing exudates from the wound site. A fourth layer is situated over the third absorbent layer for allowing limited flow of exudates from the wound site to the third layer. At least one each of an antimicrobial agent and a hemostatic agent or a multifunctional wound healing agent are each associated with the adhesive bandage in a position where the agents will come in contact with the wound site.

12 Claims, 9 Drawing Sheets

U.S. PATENT DOCUMENTS

| | | | |
|---|---|---|---|
| 4,474,769 A | | 10/1984 | Smith |
| 4,551,490 A | | 11/1985 | Doyle et al. |
| 4,616,644 A | * | 10/1986 | Saferstein et al. ............ 602/48 |
| 4,659,700 A | | 4/1987 | Jackson |
| 4,795,668 A | | 1/1989 | Krueger et al. |
| 4,803,078 A | * | 2/1989 | Sakai ........................ 424/445 |
| 4,818,464 A | | 4/1989 | Lau |
| 4,929,722 A | | 5/1990 | Partain, III et al. |
| 4,946,870 A | | 8/1990 | Partain, III. et al. |
| 4,950,709 A | | 8/1990 | Schlueter et al. |
| 4,971,956 A | | 11/1990 | Suzuki et al. |
| 5,057,368 A | | 10/1991 | Largman et al. |
| 5,061,792 A | | 10/1991 | Albisetti et al. |
| 5,069,970 A | | 12/1991 | Largman et al. |
| 5,108,820 A | | 4/1992 | Kaneko et al. |
| 5,158,555 A | | 10/1992 | Porzilli |
| 5,277,976 A | | 1/1994 | Hogle et al. |
| 5,300,494 A | | 4/1994 | Brode, II et al. |
| 5,336,552 A | | 8/1994 | Strack et al. |
| 5,382,400 A | | 1/1995 | Pike et al. |
| 5,466,410 A | | 11/1995 | Hills |
| 5,578,661 A | | 11/1996 | Fox et al. |
| 5,595,980 A | | 1/1997 | Brode et al. |
| 5,597,811 A | | 1/1997 | Gruber |
| 5,621,088 A | | 4/1997 | Gruber |
| 5,633,070 A | | 5/1997 | Murayama et al. |
| 5,736,532 A | | 4/1998 | Furda |
| 5,800,372 A | | 9/1998 | Bell et al. |
| 5,823,983 A | | 10/1998 | Rosofsky et al. |
| 6,448,462 B2 | * | 9/2002 | Groitzsch et al. ............. 602/45 |
| 2002/0111576 A1 | * | 8/2002 | Greene et al. ................ 602/42 |

OTHER PUBLICATIONS

Abstract, JP 63-041503A, Takanori et al., Feb. 22, 1988.

Abstract, JP 63-041504A, Takanori et al., Feb. 22, 1988.

Abstract, JP 08-157501A, Katakura Chikkarin KK et al., Jun. 18, 1996.

Taber's® Cyclopedic Medical Dictionary, Edition 18, F.A. Davis Co., 1997, p. 1085.

V.A. Wente et al., "Manufacture of Superfine Organic Fibers", *NRL Report* 4364 (111437), Naval Research Laboratory, Washington, D.C., May, 1954.

K.D. Lawrence et al., "An Improved Device for the Formation of Superfine, Thermoplastic Fibers", *NRL Report* 5265 (151412), Naval Research Laboratory, Washington, D.C., Feb., 1959.

A.R. Gennaro, "Medicated Topicals", *Remington: The Science and Practice of Pharmacy*, 20th Edition, Copyright 2000, by the University of the Sciences in Philadelphia, , Chapter 44, pp. 836–857.

W. Malette, H. Quigley, R. Gaines, N. Johnson, W.Rainer, "Chitosan: A New Hemostatic", *Annals of Thoracic Surgery*, vol. 36, No. 1, 1983, pp. 55–58.

R. Muzzarelli, R. Tarsi, O. Filippini, E. Giovanetti, G. Biagini, P. Varaldo, "Antimicrobial Properties of N–Carboxybutyl Chitosan", *Antimicrobial Agents and Chemotherapy*, vol. 34, No. 10, Oct. 1990, pp. 2019–2023.

R. Muzzarelli, V. Baldassarre, F. Conti, P. Ferrara, G. Biagini, "Biological Activity of Chitosan: Ultrastructural Study", *Biomaterials*, vol. 9, May 1988, pp. 247–252.

A. Tokoro, N. Tatewaki, K. Suzuki, T. Mikami, S. Suzuki, M. Suzuki, "Growth–Inhibitory Effect of Hexa–N–Acetyl-chitohexaose and Chitohexaose Against Meth–A Solid Tumor", *Chem. Pharm. Bulletin*, vol. 36, 1988, pp. 784–790.

Y. Machida, T. Nagai, K. Inouye, T. Sannan, *Chitin and Chitosan: Sources, Chemistry, Biochemistry, Physical Properties and Applications*, G. Skjak–Braek, T. Anthonsen, P. Sandford (Eds.), Elsevier Science Publishers Ltd., 1989, pp. 45–69, 101–118, 139–147, 567–576, 605–616, 657–669, 679–691.

R. Muzzarelli, C. Jeuniaux, G. Gooday, *Chitin in Nature and Technology*, Plenum Press, New York, 1986, pp. 435–460, pp. 507–512.

Y. Ohshima et al., "Clinical Application of Chitin Non-Woven Fabric as Wound Dressing", *European Journal of Plastic Surgery*, 1987, pp. 66–69.

*The Journal of the American Chemical Society*, vol. LXVII, Jul.–Dec. 1945, pp. 1184–1186.

P. Klokkevold, D. Lew, D. Ellis, C. Bertolami, "Effect of Chitosan on Lingual Hemostasis in Rabbits", *J. Oral Maxillofacial Surgery*, 1991, pp. 858–863.

J. Hokanson, P. Hayward, D. Carney, L. Phillips, M. Robson, "A Mathematical Model for the Analysis of Experimental Wound Healing Data", *Wounds*, vol. 3, No. 6, Nov./Dec. 1991, pp. 213–220.

J. Davidson, "Animal Models for Wound Repair", *Arch Dermatol Res.*, 290 (Suppl), 1998, pp. S1–S11.

J. Heggers et al., "Beneficial Effect of Aloe on Wound Healing in an Excisional Wound Model", *The Journal of Alternative and Complementary Medicine*, vol. 2, No. 2,, 1996, pp. 271–277.

K. Nishimura, I. Azuma, *Chitin Derivatives in Life Sciences*, S. Tokura, I. Azuma, (Eds.), Japan Chitin Soc., 1992, pp. 7–11.

Muzzarelli et al., "Chitosans and Other Polysaccharides as Wound Dressing Materials", *Biomedical and Biotechnological Advances*, S. Stivala, V. Crescenzi, S. Stivala (Eds.), Oct. 1988, pp. 77–88.

L. Illum, "Chitosan and Its Use as a Pharmaceutical Excipient", *Pharmaceutical Research*, vol. 15, Nov. 9, 1998, pp. 1326–1331.

D.Singh, A.Ray, "Biomedical Applications of Chitin, Chitosan, and Their Derivatives", *Rev Macromol. Chem Phys.*, C40(1), 2000, pp. 69–83.

K. Nishimura, C. Ishihara, S. Ukei, S. Tokura, I. Azuma, "Stimulation of Cytokine Production in Mice Using Deacetylated Chitin", *Vaccine*, vol. 4, Sept. 1986, pp. 151–156.

O. Felt, P. Buri, R. Gurny, "Chitosan: A Unique Polysaccharide for Drug Delivery", *Drug Development and Industrial Pharmacy*, 1998, pp. 979–993.

R. Muzzarelli et al., *Il Prodotto Chimico*, "La Cicatrizzazione Ottenuta Con Chitosani Idrosolubili", Nov. 1987, pp. 5–8.

Abstract, "Shipin Kexue", Beijing, 1987, pp. 6–9.

E. Agullo, V. Ramos, M. Varillas, *Anales De La Asociacion Quimica Argentina*, vol. 86, 1998, pp. 1–4.

K. Suzuki et al., "Antitumor Effect of Hexa–N–Acetylchi-tohexaose and Chitohexaose", *Carbohydrate Research*, 151, 1986, pp. 403–408.

U.S. Appl. No. 10/012,999, filed Nov. 13, 2001, by S. Malik for "Multicomponent Compositions Containing Chitosan and Methods of Preparing Same".

Fwu–Long Mi et al., "Fabrication and characterization of a sponge–like asymmetric chitosan membrane as a wound dressing", *Biomaterials*, England, vol. 22, No. 2, Jan. 2001, pp. 165–173.

PCT International Search Report, Dec. 9, 2002, for International Application No. PCT/US 02/29813.

* cited by examiner

BANDAGE, METHODS OF PRODUCING AND USING SAME

This case is a continuation-in-part of U.S. patent application Ser. No. 10/026,292, filed Dec. 19, 2001, and claims the priority benefit of that filing date.

FIELD OF THE INVENTION

The present invention relates to bandages and dressings for use by consumers. More particularly, the present invention relates to adhesive bandages and wound dressings for use by consumers, that promote wound healing, as well as methods of producing and using same.

BACKGROUND OF THE INVENTION

Adhesive bandages for use by the consumer to treat/dress acute wounds and/or skin irritations are not new. Adhesive bandages 10 as illustrated in FIG. 1, typically include a base layer 20, which is the layer seen by the consumer following application of the bandage to the wound. Such base layer typically has a top surface 21 and bottom surface 22, with the top surface 21 being visible to the consumer upon application to a wound. Such layer is typically formed from a polymeric material, such as a nonwoven sheet or film, or combination thereof. Such nonwoven sheets may for example be produced from meltblown and/or spunbond materials. Such film may be perforated in order to provide for some level of flexibility and breathability. A skin-friendly adhesive 30 is usually placed over the base layer bottom surface 22 to provide a means for attaching the bandage to the consumer. An absorbent pad 40 is traditionally positioned in the center of the base layer, bottom surface, for collecting exudates from a wound. Finally, a non-stick perforated layer 50 is normally positioned over the absorbent pad layer 40, to provide a barrier between the absorbent pad 40 and the wound itself, in order to provide some separation between the collected wound exudates and the wound. A release layer/sheet (not shown) is normally placed over the adhesive and other exposed bottom layers prior to use, as part of the bandage packaging, in order to keep the adhesive from adhering to a substrate for which it is not intended, as well as to protect the bandage from exposure to the environment, until the moment it is to be used. The entire bandage is packaged in a sealed enclosure for further protection. Such bandages are generally passive in nature, in that they serve merely to cover/protect a wound from exposure to the environment during the body's natural healing process.

Typically the absorbent pad in such bandage does not include any medicinal components, although comparatively recently, bandage manufacturers have started including antibiotic agents on bandages to encourage wound healing. For instance, several products are currently being marketed which contain an antiseptic benzalkonium chloride and an antibiotic mixture of polymixin B-sulfate and bacitracin-zinc. Further, patents in this area of technology have described the use of commonly known antiseptics and antibiotics, such as those described in U.S. Pat. Nos. 4,192,299, 4,147,775, 3,419,006, 3,328,259, and 2,510,993. Unfortunately, certain individuals have proven to be allergic to common antibiotics. Therefore, such bandages cannot be freely used by all consumers. Furthermore, there has recently been a push in the medical community to avoid excessive use of antibiotics so as to eliminate the risk that certain bacteria may become resistant to such medications.

There is therefore a need for an adhesive bandage which does not utilize traditional antibiotic treatment, but which does promote wound healing. Furthermore, there is a need for an adhesive bandage which promotes wound healing in multiple ways, but which does not utilize agents which may cause an allergic response in certain individuals. There is also a need for adhesive bandages which promote wound healing through the use of naturally occurring and readily available substances, and that will not add significantly to the price that consumers will pay for such bandages. Still further, there is a need for multifunctional bandages which perform numerous wound healing functions with one wound healing composition.

It has not been new for bandages to accomplish hemostatic functions. For instance, WO99/59647 describes a multilayered haemostatic bandage which comprises preferably a thrombin layer between two fibrinogen layers. The dressing may contain other resorbable materials such as glycolic acid or lactic acid based polymers or copolymers. A hemostatic bandage is also disclosed in WO97/28832. As in the previous reference, such bandage utilizes thrombin, in connection with fibrinogen, adhered to a fibrous matrix. While such bandages absorb fluid, they are directed to a hemostatic function primarily.

U.S. Pat. No. 5,800,372 describes a field dressing for control of exsanguination. Such dressing describes the use of microfibrillar collagen and a superabsorbent polymer in a hemostatic bandage, which both absorbs blood and induces clotting. Again, as in the prior example, such bandage is directed to the primary function of inducing coagulation.

The compound chitosan is a deacetylated product of chitin $(C_8H_{13}NO_5)_n$, an abundant natural glucosamine polysaccharide found in the ecosystem. In particular, chitin is found in the shells of crustaceans, such as crabs, lobsters and shrimp. The compound is also found in the exoskeletons of marine zooplankton, in the wings of certain insects, such as butterflies and ladybugs, and in the cell wall of yeasts, mushrooms and other fungi.

In addition to being non-toxic, biocompatible and biodegradable, chitosan is also reported in the scientific literature to possess hemostatic, antimicrobial properties and other biomedical attributes. See for instance, *Rev Macromol. Chem Phys.*, C40, 69–83 (2000), *Chitin and Chitosan*, Editors, G. Skjak-Braek, T. Anthonsen and P. Sanford, Elsevier, (1988); *Chitin in Nature and Technology*, Editors, R. Muzzarelli, C. Jeuniaux and G. W. Gooday, Plenum Press, (1986).

The biocompatibility of chitosan administered orally and intravenously has been assessed in animals. Its $LD_{50}$ is over 16 g/Kg in mice, which is higher than for sucrose. $LD_{50}$ is traditionally defined as the median lethal dose of a substance, which will kill 50% of the animals receiving that dose, with the dose being calculated on amount of material given per gram or kilogram of body weight, or amount per unit of body surface area. See for instance, the $18^{th}$ Edition of *Taber's Cyclopedic Medical Dictionary*, p. 1085. The hemostatic properties of Chitosan have also been evaluated in the scientific literature in publications such as *Ann. Thor. Surg.*, 35, 55–60, (1983); *J Oral Maxillof Surg*, 49, 858–63, (1991).

In recent years, however, attention has been directed in the research community towards biomedical applications of the chitosan compound. In this regard, the use of chitosan in the pharmaceutical and healthcare industry is currently being evaluated. For instance, use of chitosan has been reported in a pharmaceutical product in *Pharm Res*, 15, 1326–31, (1998). The use of chitosan in the pharmaceutical industry as an excipient has also been explored in *Pharm*

Res, 15, 1326–31, (1998) and *Drug Dev. Ind Pharm*, 24, 979–93, (1998).

Antimicrobial properties of chitosan have been reported against Gram positive and Gram negative bacteria, including *Streptococcus* spp., *Staphylococcus aureus, Staphylococcus epidermidis, Staphylococcus haemolyticus, Pseudomonas, Escherichia, Proteus, Klebsiella, Serratia, Acinobacter, Enterobacter* and *Citrobacter* spp. See for instance, Muzzarelli et al., in *Industrial Polysaccharides: Biomedical and Biotechnological Advances*, Eds., V. Crescenzi and S. S. Stivala, *Gordon and Breach*, pp. 77–88, (1990) and *Antimicr. Agents Chemoth.*, 34, 2019–24, (1990). See also, U.S. Pat. No. 4,659,700, which describes the use of Chitosan in a gel to be applied to wounds.

Chitosan has also been described in the literature to induce repair of tissue containing regularly arranged collagen bundles. See for instance *Biomaterials*, 9, 247–52, (1988). Additionally, non-woven fabrics made of chitosan fibers have been developed. See for instance, *Eur. J. Plastic Surg.*, 10, 66–76, (1987).

Further, chitin and chitosan derivatives have been studied for their antitumor effects. See for instance, *Carbohydr. Res*, 151, 403–8, (1986); and *Chem. Pharm*, 36, 784–90, (1988). Chitosan has additionally been reported as an effective immunomodulator in *Vaccine*, 4, 151–6, (1986); and K. Nishimura in *Chitin Derivatives in Life Sciences*, Ed., S. Tokura, Japan Chitin Soc., (1992). Despite all of the research in the chitosan area, there is still a need for a practical application of chitosan that can benefit individuals on a daily basis, such as in the application to acute wounds obtained during a person's daily routine.

While nicotinic acid (niacin), niacinamide (vitamin B3), ascorbic acid and niacinamide ascorbate are known as dietary supplements, for a variety of functions, it is not believed that such uses have been in conjuction with epidermal wound healing functions.

SUMMARY OF THE INVENTION

The present invention addresses some of the difficulties and problems discussed above by providing an adhesive bandage with both antimicrobial and hemostatic properties. Desirably the adhesive bandage is of the type used on acute wounds, burn wounds and irritations and includes a first layer for covering the wound site and an area around the wound site. The first layer includes a top surface and bottom surface. A second adhesive layer is situated over the first layer bottom surface, for adhering the adhesive bandage to a wound site. A third absorbent layer is situated over the second layer, for absorbing exudates from the wound site. A fourth layer is situated over the third absorbent layer for allowing limited flow of exudates from the wound site to the third layer. At least one each of an antimicrobial agent and a hemostatic agent or a single wound healing agent with hemostatic and antimicrobial functionality, are each associated with the adhesive bandage in a position where the agents will come in contact with the wound site, which are transferable from the adhesive bandage to the wound site. Desirably in one embodiment, the antimicrobial agent and hemostatic agents are incorporated into the one compound Chitosan niacinamide ascorbate.

The present invention further provides a method of producing an adhesive bandage for treating acute wounds, burn wounds and irritations consisting of the steps of a) providing an adhesive bandage which includes a first layer for covering the wound site and an area round the wound site; a second adhesive layer over the first layer, for adhering the adhesive bandage to a wound site; a third absorbent layer over the second layer, for absorbing exudates from the wound site; a fourth layer over the third absorbent layer for allowing limited flow of exudates from the wound site to the third layer; and b) treating either the absorbent layer, the fourth layer or both layers, so as to include at least a hemostatic agent and an antimicrobial agent, or a single wound healing agent, which agents which are transferable from the layer or layers to the wound site.

The present invention still further provides a method of producing an adhesive bandage for treating minor wounds cuts or abrasions consisting of the steps of a) providing an adhesive bandage which includes a first base layer for covering the wound site and an area around the wound site; b) coating an adhesive layer over said first layer, for adhering the adhesive bandage to a wound site; c) adhering a third absorbent layer over the second layer, for absorbing exudates from a wound site; the absorbent layer including either a hemostatic agent, antimicrobial agent or both, for transferring to a wound; and d) adhering a fourth layer over the third absorbent layer for allowing limited flow of exudates from a wound site to the third absorbent layer, as well as transference of either the hemostatic agent and the antimicrobial agent to a wound.

The present still further provides a method of producing an adhesive bandage for treating acute wounds, burn wounds and irritations consisting of the steps of: a) providing an adhesive bandage which includes a first base layer for covering the wound site and an area around the wound site; b) coating an adhesive layer over the first layer, for adhering the adhesive bandage to a wound site; c) adhering a third absorbent layer over the second layer, for absorbing exudates from a wound site; and d) adhering a fourth layer over the third absorbent layer, the fourth layer including either a hemostatic agent, antimicrobial agent or both, for transferring to a wound; and wherein the fourth layer allows limited flow of exudates from a wound site to the third absorbent layer, as well as transference of the hemostatic agent and the antimicrobial agent to a wound.

These and other features and advantages of the present invention will become apparent after a review of the following detailed description of the disclosed embodiments and the appended claims.

DETAILED DESCRIPTION OF THE INVENTION

Figure 1:
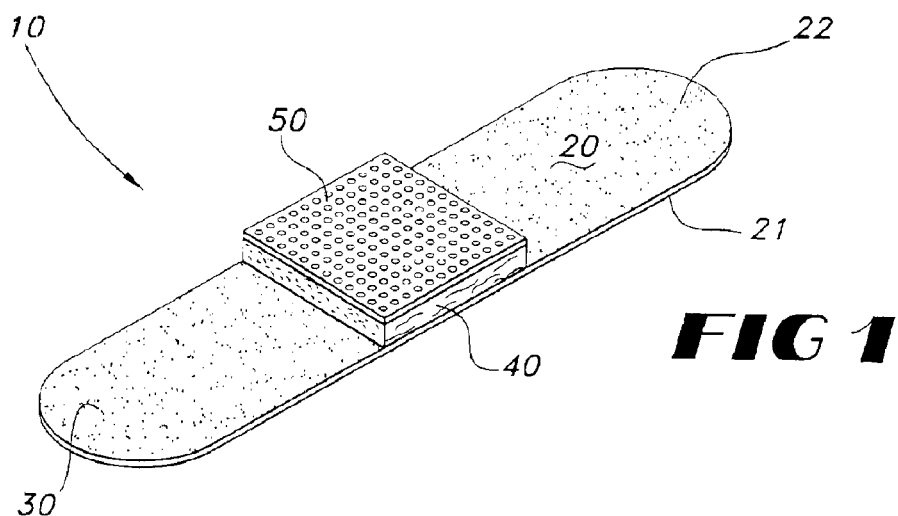
FIG. 1 is a perspective view of a bandage of the prior art.

Definitions:

For the purposes of this application the term "antimicrobial agent" shall refer to a compound which stops, prevents, or destroys the growth of microorganisms.

For the purposes of this application, the term "hemostatic agent" shall refer to a compound which reduces blood clotting time.

For the purpose of this application, the term "naturally occurring compounds" shall refer to compounds which can be found in nature, such as from soil, marine life, plants and terrestrial organisms.

As used herein, the term "bandage" shall be used interchangeably with "wound dressing" and "dressing", and shall refer to a covering to be placed over a wound.

As used herein, the term "transferable" shall be interchangeable with "releasable", and shall refer to the ability of a substance to be passed from a substrate such as a bandage, bandage layer or component, to a wound, through contact with the wound.

As used herein, the term "acute wound" shall refer to a wound caused by a traumatic abrasion, laceration or through superficial damage, and which heals spontaneously without complications through normal phases of wound healing (such as hemostasis, inflammation, proliferation and remodeling).

As used herein, the term "chronic wound" shall refer to a wound in which there is no clot formation, normally occurring in patients who are compromised in some fashion who are less likely to heal. When the body's natural healing process is delayed due to an underlying pathological process, such as a vascular insufficiency, it may lead to a chronic wound.

As used herein, the term "partial thickness wound" shall refer to a wound that is limited to the epidermis and superficial dermis with no damage to the dermal blood vessels.

As used herein, the term "full thickness wound" shall refer to a wound that involves total loss of epidermal and dermal layers of the skin, extending at least to the subcutaneous tissue layer and possibly as deep as the fascia-muscle layer and the bone.

As used herein, the term "nonwoven web" means a polymeric web having a structure of individual fibers or threads which are interlaid, but not in an identifiable, repeating manner. Nonwoven webs have been, in the past, formed by a variety of processes such as, for example, meltblowing processes, spunbonding processes, hydroentangling, air-laid and bonded carded web processes.

As used herein the term "spunbond" refers to small diameter fibers which are formed by extruding molten thermoplastic material as filaments from a plurality of fine, usually circular capillaries of a spinneret with the diameter of the extruded filaments being rapidly reduced as by for example in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,542,615 to Dobo et al.

As used herein the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al.

As used herein the term "sheet material" refers to nonwoven webs, polymeric films, polymeric scrim-like materials, and polymeric foam sheeting. The term film shall include breathable and non-breathable monolithic film, porous, and non-porous film, and apertured and non-apertured film.

As used herein the term "laminate" refers to a composite structure of two or more sheet material layers that have been adhered through a bonding step, such as through adhesive bonding, thermal bonding, point bonding, pressure bonding or ultrasonic bonding.

As used herein the terms "elastic" and "elastomeric" refers to sheet material which, upon application of a biasing force, is extensible or elongatable in at least one direction.

As used herein, the term "inelastic" or "nonelastic" refers to any material which does not fall within the definition of "elastic" above.

As used herein, the term "coform" means a process in which at least one meltblown diehead is arranged near a chute through which other materials are added to the web while it is forming. Such other materials may be pulp, superabsorbent particles, cellulose or staple fibers, for example. Corform processes are shown in commonly assigned U.S. Pat. No. 4,818,464 to Lau and U.S. Pat. No. 4,100,324 to Anderson et al. each incorporated by reference in their entirety.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

Reference now will be made in detail to the embodiments of the invention, one or more examples of which are set forth below. Each example is provided by way of explanation and not limitation of the invention. It will be apparent to those of ordinary skill in the art that various modifications and variations can be made in the present invention without departing from the spirit and scope of the invention. It is intended that the present invention covers such modifications and variations as come within the scope of the appended claims and equivalents.

Figure 2:
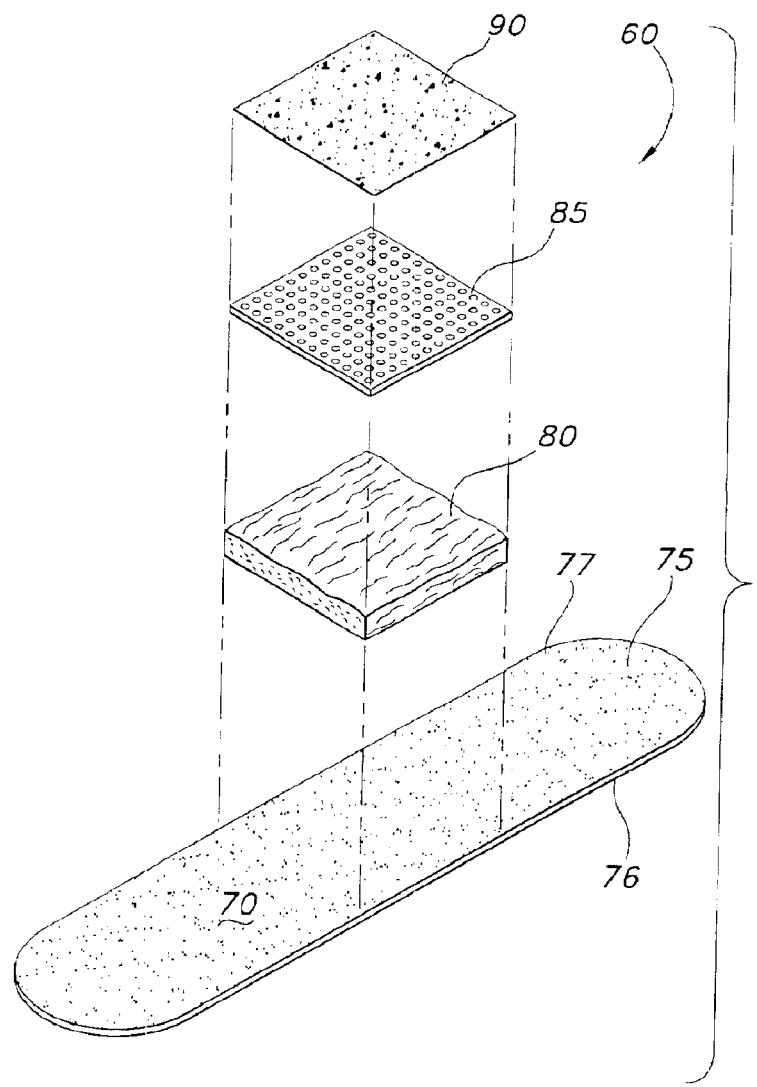
FIG. 2 is an exploded perspective view of a bandage in accordance with the present invention.

As can be seen in FIG. 2, for use in a bandage, the present invention is generally directed to a bandage 60 for acute wounds, consisting of a base sheet 70 having a bottom side surface 75 and a top side surface 76 which is that surface seen by a consumer after application of the bandage to the wound site. In one embodiment, the base sheet is desirably elastomeric. In a further embodiment, the base sheet has been coated with a suitable skin-friendly adhesive 77, along its skin contacting surface (bottom side surface 75). It should be appreciated that this is not necessary if it is not desired that the base sheet be applied to a wound via its own adhesive. In this instance, separate adhesive tape may be used. The elastomeric base sheet may be comprised of nonwoven and film-based polymeric materials or combinations thereof, for example, such as those materials described in U.S. Pat. Nos. 3,976,563 and, 5,633,070 which are incorporated by reference herein in their entirety. Such base sheets are made by methods known in the art, and described in the heretofore mentioned patents. The elastomeric base sheet may be a breathable monolithic film or a perforated film, to provide for some level of flexibility around a joint (if appropriate) and some level of breathability. Alternatively, the base sheet/backing material may be a nonwoven material, or a combination of a nonwoven material and a film. If present, the adhesive may be any skin-friendly adhesive known in the art, such as rubbery adhesives, acrylic adhesives, polyurethane adhesives, silicone adhesives, and block copolymer adhesives and those described in U.S. Pat. Nos. 4,147,831, 4,551,490, and EPO 361 72291, EP 1008330A2 and WO 00/12038 which are incorporated by reference herein in their entirety. The base sheet includes along its skin contacting surface (bottom side layer), an absorbent layer 80 (or absorbent pad).

The elastomeric base sheet includes along its skin contacting surface (the bottom surface), an absorbent layer in the form of an absorbent pad 80, that is situated generally in the center of the base sheet over the adhesive layer. The absorbent layer is desirably made up of either cellulosic wadding or nonwoven material, as described in the previous references. Other suitable absorbent pads include nonwoven materials that have been treated to be hydrophilic. The absorbent pad is desirably covered with a non-stick perforated cover 85. The perforated cover is desirably a perforated film that has been laminated to the absorbant pad. Such lamination may be by adhesive or other bonding means. Desirably, the film is a Delnet polyethylene film, available from AET of Delaware. Desirably, the perforated nonstick cover has associated along its outer layer (not in contact with the absorbent pad) on the skin contacting surface, a combination of at least one antimicrobial agent, and at least one hemostatic agent shown generally as 90. Desirably, the antimicrobial agent(s) and hemostatic agent(s) are selected from naturally occurring compounds commonly found in fruit, vegetables, herbs and spices. For instance, such wound healing, antimicrobial and hemostatic agent(s) are desirably selected from the group consisting of chitosan niacinamide ascorbate salt, niacinamide ascorbate, and chitosan, or combinations thereof. More desirably, such antimicrobial agent and hemostatic agent are found in one multifunctional wound healing agent. Such a single multifunctional agent is exemplified by chitosan niacinamide ascorbate salt. As has been indicated previously, one or more of these wound healing antimicrobial agents can be used on the bandage itself. Such agents may be placed in any location within or on the bandage, bandage layers, or bandage components that are in contact with the wound site. For instance, such agents may be coated on the bandage or bandage layers, such as on the absorbent layer or nonstick perforated barrier layer 85 ( if it is present), or impregnated in the bandage or bandage layers, such as in the absorbent layer 60.

As a further alternative embodiment, the wound healing antimicrobial agent and hemostatic agents, or single agent with multifunctional attributes, may be incorporated into a topical cream or lotion, applied to the wound site as such, and then covered with a prior art bandage (either adhesive or nonadhesive). Such topical lotions and the preparation of such are described in *Remington: The Science and Practice of Pharmacy,* 20$^{th}$ *Edition, Gennaro Editor,* 2000. In particular, one should refer to Chapter 44, pages 836–857, which is incorporated by reference herein in its entirety.

Again, as has been previously indicated, one or more of the hemostatic agents can be used on the bandage itself. Desirably, each of the wound healing antimicrobial agents and hemostatic agents will be selected from "GRAS" compounds, that is compounds that are "generally regarded as safe". Desirably the wound healing antimicrobial and hemostatic agent are incorporated into the one compound Chitosan niacinamide ascorbate.

Such wound healing antimicrobial agents may be applied to the non-stick perforated layer as a treatment, such as being applied as a spray or by printing during the film manufacturing process, or in the alternative, such materials may be extruded as part of the film. It should be recognized that the non-stick perforated layer is optional, and that such wound healing agents may instead be incorporated into other bandage layers, such as the absorbent pad layer.

In such instance, such wound healing agents would then be released either through the perforated film layer to the wound from the absorbent pad, or directly from the absorbent pad to the wound. In either even, it is desirable that the wound healing hemostatic agents and antimicrobial agents be placed on the adhesive bandage in a position where such agents will come in contact with the wound. Such contact can be either via direct contact with an outer layer of the adhesive bandage that is in direct contact with the wound, or in the alternative by being released from one of the bandage layers into the wound.

Desirably an effective amount of the wound healing antimicrobial and hemostatic agent is associated with the bandage. Such is desirably an amount that produces an increase in re-epithialization rates.

For the purposes of this application, and as a preliminary matter, a series of hemostatic agents were evaluated in order to determine a relative comparison of the effectiveness of such compounds on human blood. Each of the compounds were evaluated in the comparison against the standard control (human blood) and the negative control heparin, which is an anti-coagulant. The results of the study are shown in Table I which follows. As can be seen in the data of Table I, Chitosan niacinamide ascorbate produced the shortest coagulation time of any of the compounds evaluated.

Preliminary Review of Hemostatic Agents
Lee and White Coagulation Assay in Human Blood

TABLE I

| COMPOUNDS | BLOOD CLOTTING TIME (MIN) |
| --- | --- |
| Chitosan niacinamide ascorbate | 8.83 ± 0.28 |
| Chitosan | 9.00 ± 0.50 |
| Sodium alginate (Granular, Aldrich) | 9.33 ± 0.28 |
| Untreated blood (control) | 10.16 ± 0.28 |
| Heparin (negative control for comparison) | NC |

NC = No Clot for 60 min
All tests were run in triplicate and samples were used in dried form (5 mg/ml)

Study of Control Bandage Material and Test Compounds

Following the assessment of hemostatic agents, a study was conducted using the accelerated wound healing study protocol which follows. In the examples of the study, a series of comparative control bandage substrates were evaluated as to the speed at which wounds covered/dressed with such bandages healed. In particular, the rates of re-epithelialization were measured for wounds dressed by such control dressing materials. Additionally, the rates at which wounds heal that have been treated with a series of test compounds in accordance with the present invention, were also measured and compared with the controls.

For the purposes of the examples, the test compounds consisted of chitosan, Niacinamide ascorbate (hereinafter NA) prepared by the method which follows; and chitosan niacinamide ascorbate salt (hereinafter CNA, prepared by the method which follows), 2-ply surgical gauze, and Comfeel® Plus Clear Dressing (Colorplast).

Wounds were treated with test and control articles on the day of wounding (day 0) on 2, 4, 6, 8, 10, 12, and 14 days after the injury. CNA (freeze dried) was cut to the approximate size of the wound and applied over the wound. Chitosan (powder) and NA (powder) were applied over the wound to the depth that covered the underlying tissue. The gauze was cut to extend approximately 0.5 cm beyond the margins of the wound. The Comfeel® Plus dressing was cut to the approximate size of the wound and applied over the wound and also used to cover all test and control articles over the entire dorsal surface of the animal.

Specifically, these examples illustrate the effects of test compounds on wound healing in a rat model, as described in J. M. Davidson, *Arch Dermatol Res.*, 290 (Suppl): S1–S11, 1998; J. P. Heggers et al., *J Altern Compl Med.*, 2,271–77, 1996; J. A. Hokanson et al., *Wounds*, 3, 213–220, 1991, which describe such testing protocols, and which are incorporated herein by reference in their entirety.

For the study, twenty four albino rats (12M/12F), each weighing between 250–300 g, were anesthetized (90 mg/Kg Ketamine HCL and 10 mg/Kg Xylazine) and the entire dorsal region of each rat was shaved. Four wounds measuring 1.4 cm$^2$ were made on the dorsal skin, two on either side of the vertebral column, with a rotary dermabrasion device (Dermatome). The wounds were made to a depth to yield full thickness (excisional) wounds. The test compounds and control bandages were applied topically to cover the entire wound. Test compounds and control dressings were distributed among three animals of each sex per time point (1, 2, 5, 10, 15 days), such that each test and control was applied twice/sex/time point. Four rats (2M/2F) were sacrificed at each time point and morphometric analysis was used to assess the re-epithelization of each wound at each time point. At each time of sacrifice, each wound was excised with 5 mm margin of uninjured tissue as a border. Sections were cut in cross sections encompassing the entire wound and began at the margin of the initial wound and proceeded in 3.5 mm increments across the width of the wound. The epithelial thickness of the three sections of the wound (margin, center and midpoint between these two) was measured by morphometric analysis of the microscopic image using Image-Pro Plus software, Version 3.0 (Media Cybernetics). The average thickness of these sites within the wound was determined for wound healing of the entire site. The rate of epithelization at the test and control sites was plotted vs time and presented in FIGS. 3–10.

Preparation of NA and CNA for the Study

Niacinamide ascorbate (0.87 g, 0.0029 moles) was prepared by mixing equimolar amounts of niacinamide (Sigma Chemical of St. Louis, Mo.) and ascorbic acid (Sigma Chemical) as reported earlier by C. W. Bailey et al., *J Amer. Chem. Soc.*, 67, 1184–5, (1945), was dissolved in 60 ml H$_2$O (pH of 3.85 at 20.9° C.). The solution was stirred for ten minutes and chitosan (0.5 g, degree of deacetylation 78.8%, 0.0029 moles) (Vanson, Inc. Redmond, Wash.) was added to the solution. The solution was stirred for 3 hrs to give a clear solution (pH of 4.62 at 21.4° C. of chitosan niacinamide ascorbate salt (C N A)). The pH of the solution was adjusted to 5.6 by adding chitosan (0.4 g) in 20 ml water. The material was dried by freeze drying. It should be noted that NA is also commercially available commercially from the Spectrum Laboratory Products, Inc., Gardena, Calif. Following completion of the study, the data was analyzed and graphed as follows.

Results of Study

Figure 3:
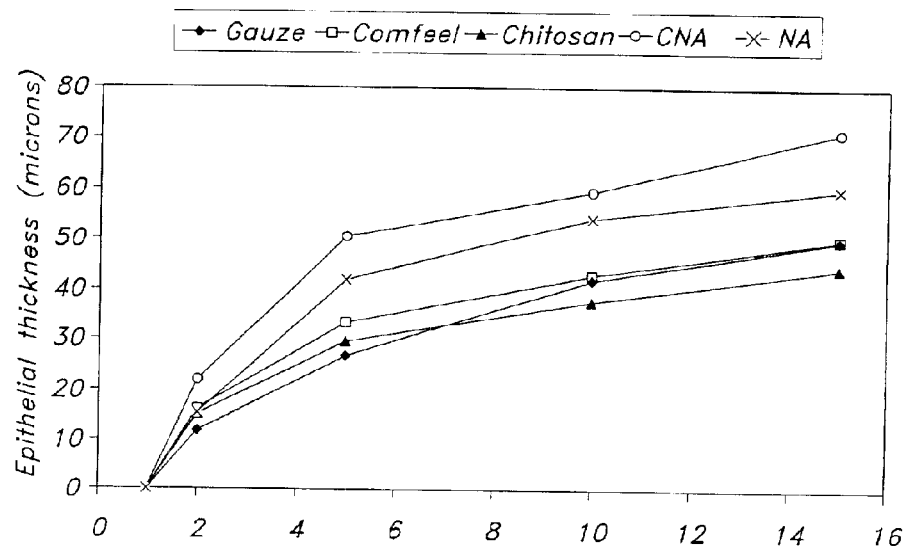
FIG. 3 is a graph illustrating accelerated wound healing data in the full thickness acute wound model, specifically showing the epithelial thickness of rats over a period of 15 days following treatment with two controls and three test compounds.

FIG. 3 is a graph illustrating accelerated wound healing in the full thickness acute wound model, showing the epithelial thickness of rats over a period of 15 days. In the graph, the rate of epithelialization in thickness (microns) is compared for five materials, include the two controls gauze and Comfeel®, and the test compounds Chitosan, CNA and NA. The evaluation of thickness change was monitored over a period of 15 days.

Figure 4:
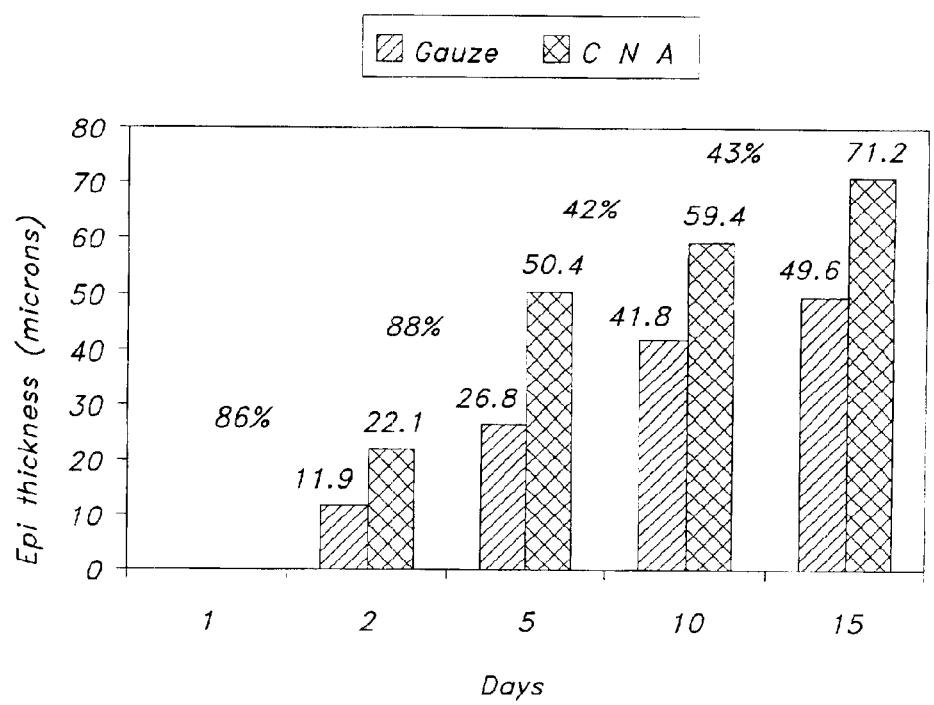
FIG. 4 is a graph illustrating accelerated wound healing data for a gauze control and the Chitosan niacinamide ascorbate test compound over a period of 15 days.

As can be seen in FIG. 4 illustrating a graph showing accelerated wound healing in the full thickness acute wound, specifically showing the epithelial thickness of rats in the gauze control and the CNA test compound over a period 15 days. In the figure, the differences in epithelial thickness is compared between CNA and the gauze control, one of two controls used in the study. The test compound CNA demonstrated improved thickness over the control. The maximum difference between the control and the test compound is seen on days 2 and 5. On day 2 and day 5, the improvement is about 86–88% over the control. On days 10 and 15, as the natural healing process has initiated on its own, the differences between the control and the test compound is reduced to between 42 and 43%. It should also be noted that on day 5, the epithelial thickness with the CNA is about 50 microns. In order for the control to reach the 50 micron level of thickness, it took approximately 15 days. Therefore, almost a 300% faster rate or re-epithelialization is demonstrated with CNA over the control, in terms of time. Similarly, the epithelial thickness with CNA on day 2 is about 22 microns, and it takes approximately twice the time with the control to achieve the same level of thickness.

Figure 5:
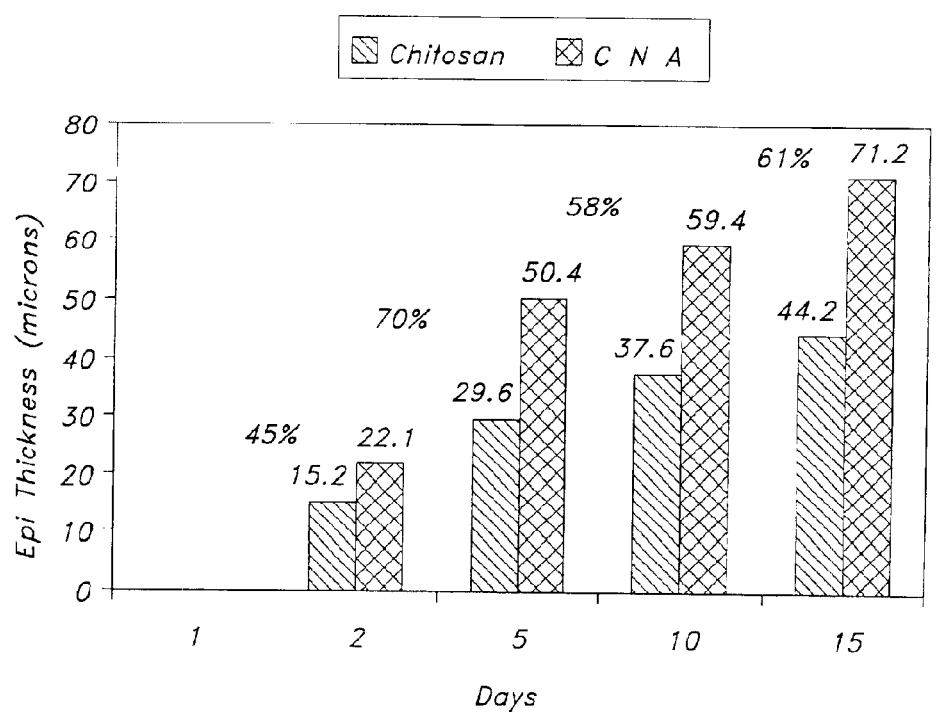
FIG. 5 is a graph illustrating accelerated wound healing data for the two test compounds chitosan and Chitosan niacinamide ascorbate over a period of 15 days.

As can be seen in FIG. 5, illustrating a graph comparison of the two test compounds chitosan and CNA and their effects on epithilial thickness over a period of time, the maximum improvement is observed on day 5, where the difference between epithelial regeneration is about 70%, with CNA being of the higher value. Overall, the data demonstrated a steady improvement rate in both materials.

The data also seems to indicate that Chitosan alone is not responsible for accelerated wound healing, and that it is the synergistic effect of chitosan with a substance which appears to be responsible for the wound healing rates.

Figure 6:
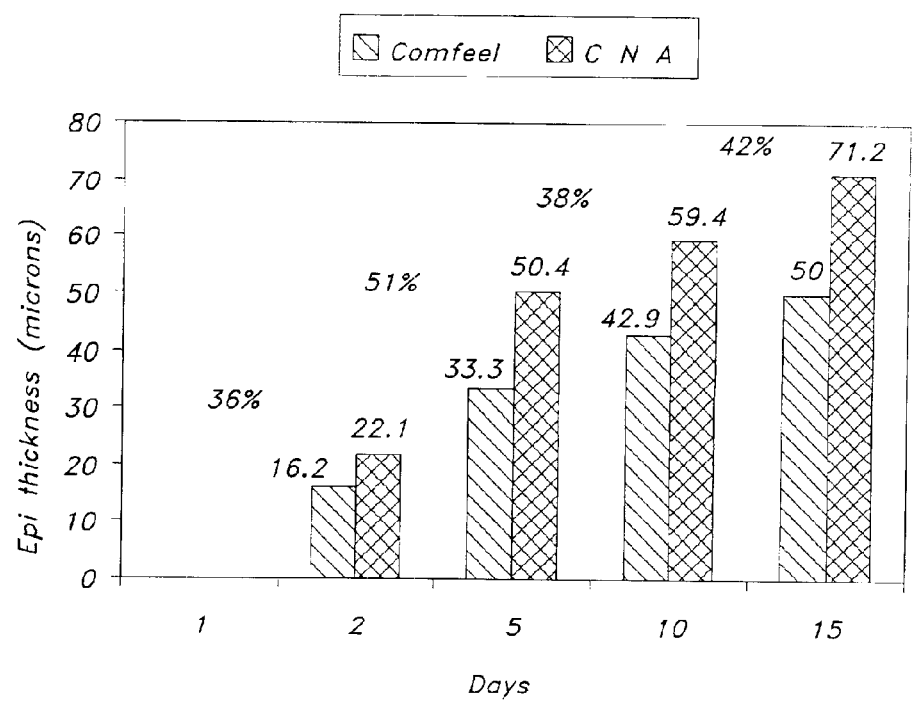
FIG. 6 is a graph illustrating accelerated wound healing data for the Comfeel® control and the Chitosan niacinamide ascorbate test compound over a period of 15 days.

As can be seen in FIG. 6, which shows the accelerated wound healing for the Comfeel® control and the test compound CNA over a period of 15 days, the Comfeel® Plus (from Colorplast), which is often used as an ulcer dressing, is compared with the CNA test compound, and the CNA compound shows the faster rate of re-epithelialization when compared with the Comfeel®. Again, as in the previous graphs, the most obvious difference is seen on day 5. The epithelial thickness of the CNA is about 50 microns, whereas the epithelial thickness for the Comfeel® is about 33 microns.

Figure 7:
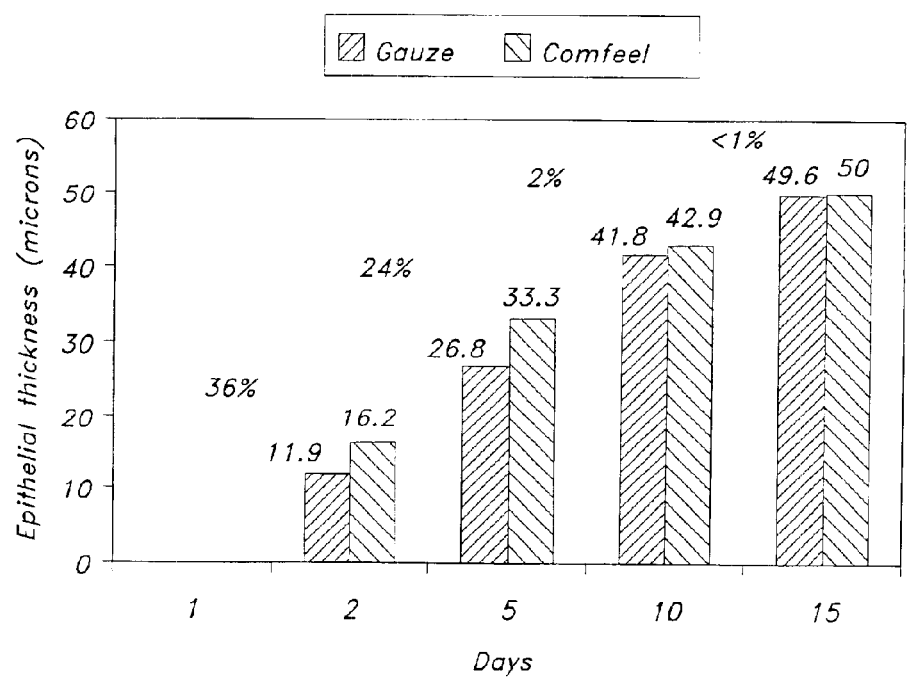
FIG. 7 is a graph illustrating accelerated wound healing data for the gauze and Comfeel® control samples over a 15 day period.

As can be seen in FIG. 7 which illustrates accelerated wound healing data for the gauze and Comfeel® control samples over a 15 day period, the Comfeel® control has demonstrated faster rates of re-epithelialization on day 2 and day 5, but on the later dates, there are only small differences observed. It is also evident from the data, that the improvement in rate of re-epithelialization by the Comfeel® control over the gauze control, is not as large as that of the improvement of the CNA test compound over the gauze.

Figure 8:
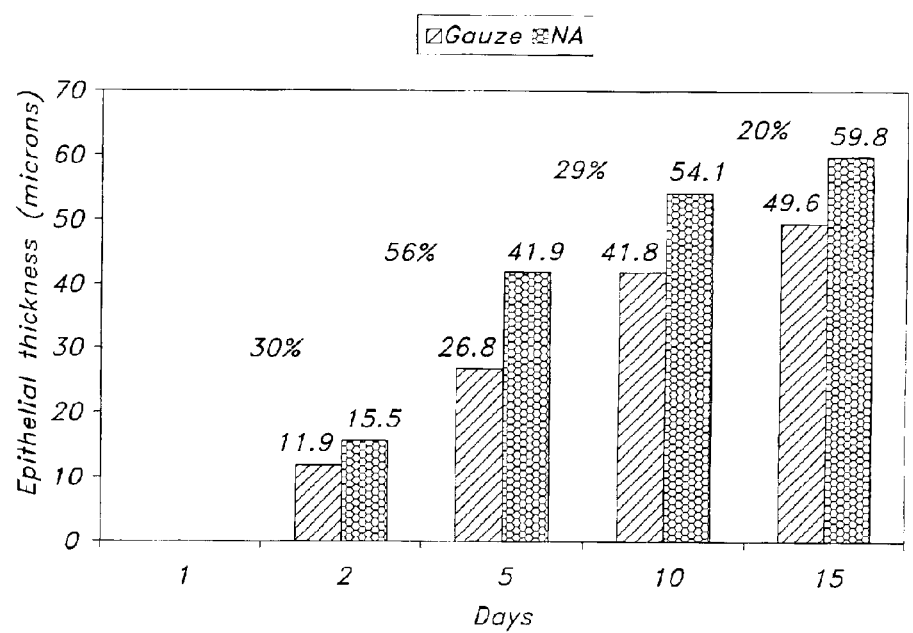
FIG. 8 is a graph illustrating accelerated wound healing data for the gauze control samples and the Niacinamide ascorbate test compound over a period of 15 days.

As can be seen in FIG. 8, which illustrates a comparison of accelerated wound healing data for the gauze control samples and that of the NA test compound over a period of 15 days, the NA test compound shows larger numbers for re-epithelialization than the control. In particular, on day 5, the test compound NA is demonstrating more than a 50% improvement over the control.

Figure 9:
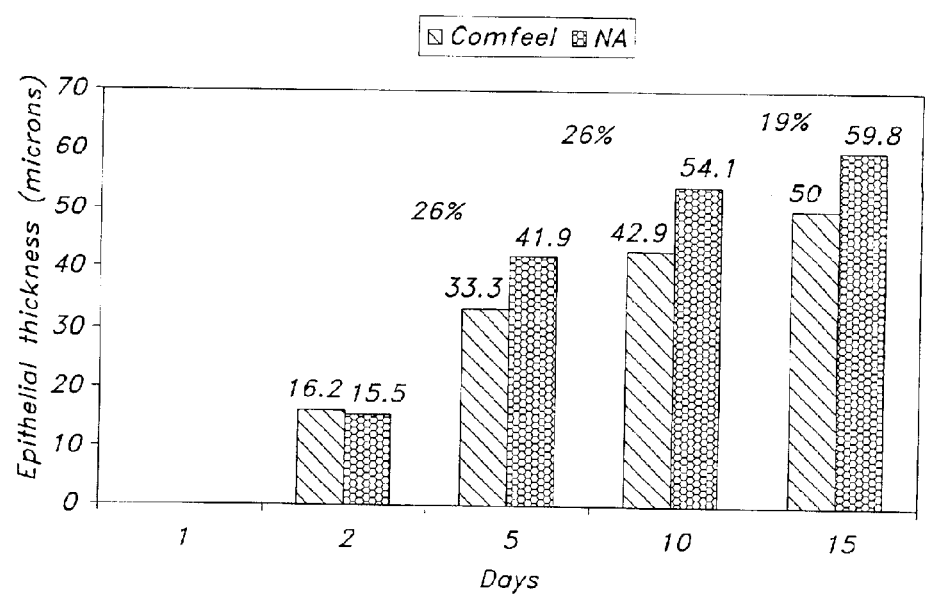
FIG. 9 is a graph illustrating accelerated wound healing data for the Comfeel® control samples and the Niacinamide ascorbate test compound over a period of 15 days.

As can be seen in FIG. 9, which illustrates a comparison of accelerated wound healing data for the Comfeel® control samples and that of the NA test compound, from day 5 through day 15 the NA test compound produced larger growth rates (re-epithelialization rates) than the Comfeel® material, despite the fact that on day 2 there was only minor differences between the two.

Figure 10:
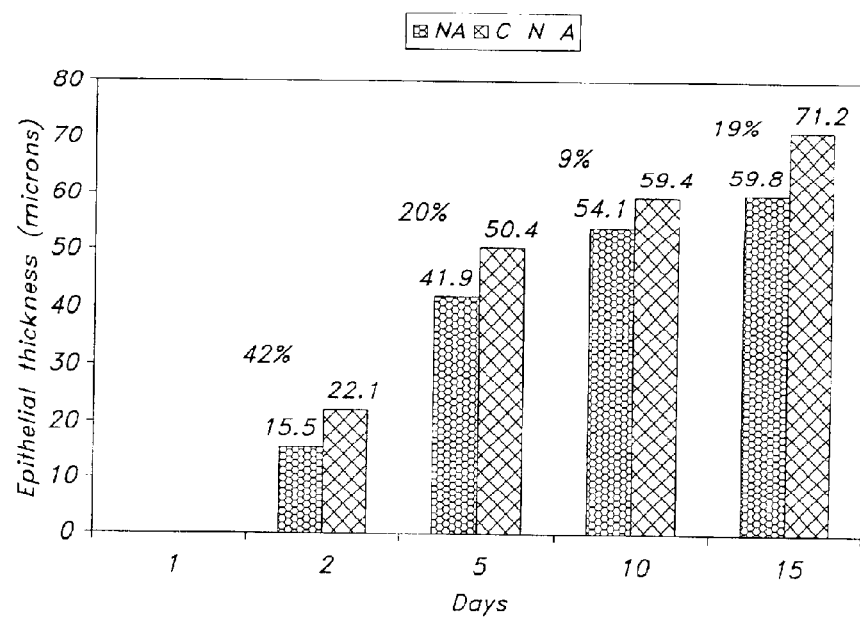
FIG. 10 is a graph illustrating accelerated wound healing data for the Niacinamide ascorbate and Chitosan niacinamide ascorbate test compounds over a period of 15 days.

As can be seen in FIG. 10, which illustrates a comparison of accelerated healing data for the NA and CNA test compounds, while each seem to demonstrate larger growth rates than the control samples, CNA appears to demonstrate larger wound healing in terms of re-epithelialization than the NA.

It should be noted that in each of the graphs the percent difference comparisons between samples is listed above the various bars in the graphs.

Given the increased rate of re-epithelialization using such wound healing antimicrobial and hemostatic agents, it is surmised that use of such agents as part of a contact surface in an adhesive bandage would likewise increase rates of wound healing in acute wounds, burn wounds and irritations covered by such bandages.

An adhesive bandage has therefore been described which utilizes naturally occurring substances to improve the healing processes of a wound, by accelerating the wound healing process. Such naturally occurring substances are less likely to be toxic to certain individuals than antibiotic treatment.

Although various embodiments of the invention have been described using specific terms, devices, and methods, such description is for illustrative purposes only. The words are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. An adhesive bandage of the type used on acute wounds, burn wounds and irritations comprising:
   - a first layer for covering the wound site and an area around the wound site, said first layer including a top surface and bottom surface;
   - a second adhesive layer over said first layer bottom surface, for adhering the adhesive bandage to a wound site;
   - a third absorbent layer over said second layer, for absorbing exudates from the wound site;
   - a fourth layer over said third absorbent layer for allowing limited flow of exudates from the wound site to the third layer; and
   - at least one each of a wound healing antimicrobial agent and a hemostatic agent, or a single wound healing agent with antimicrobial and hemostatic functionality, selected from the group consisting of chitosan niacinamide ascorbate salt, niacinamide ascorbate, and combinations thereof, each agent associated with said adhesive bandage in a position where said agent will come in contact with the wound site, and which are transferable from the adhesive bandage to the wound site.

2. The adhesive bandage of claim 1 wherein said multifunctional wound healing agent is chitosan niacinamide ascorbate salt.

3. The adhesive bandage of claim 1 wherein said multifunctional wound healing agent is a mixture of chitosan, niacinamide, and ascorbic acid.

4. The adhesive bandage of claim 1 wherein at least one of said wound healing antimicrobial agent and said hemostatic agent are located in a coating layer over said fourth layer.

5. The adhesive bandage of claim 1, wherein at least one of said wound healing antimicrobial agent and said hemostatic agent are located within said absorbent layer.

6. The adhesive bandage of claim 1, wherein at least one of said third or fourth layers is made from, or includes a treatment of either a wound healing hemostatic agent, antimicrobial agent or both.

7. A method of producing an adhesive bandage for treating acute wounds burn wounds and irritations, consisting of the steps of:
   a) providing an adhesive bandage which includes
      - a first layer for covering the wound site and an area around the wound site;
      - a second adhesive layer over said first layer, for adhering the adhesive bandage to a wound site;
      - a third absorbent layer over said second layer, for absorbing exudates from the wound site;
      - a fourth layer over said third absorbent layer for allowing limited flow of exudates from the wound site to the third layer; and
   b) treating either the absorbent layer, the fourth layer or both layers, so as to include at least one each of a wound healing hemostatic agent and an antimicrobial agent or a single wound healing agent with hemostatic and antimicrobial multifunctionality, selected from the group consisting of chitosan niacinamide ascorbate salt, niacinamide ascorbate, and combinations thereof. which agent(s) are transferable from the adhesive bandage to the wound site.

8. The method of claim 7, wherein said wound healing agent is chitosan niacinamide ascorbate salt.

9. The method of claim 7, wherein said wound healing agent is a mixture of chitosan, niacinamide, and ascorbic acid.

10. A method of producing an adhesive bandage for treating acute wounds, burn wounds and irritations consisting of the steps of:
   a) providing an adhesive bandage which includes
      a first base layer for covering the wound site and an area round the wound site;
   b) coating an adhesive layer over said first layer, for adhering the adhesive bandage to a wound site;
   c) adhering a third absorbent layer over said second layer, for absorbing exudates from a wound site; said absorbent layer including either a hemostatic agent, antimicrobial agent or both, selected from the group consisting of chitosan niacinamide ascorbate salt, niacinamide ascorbate, and combinations thereof, for transferring to a wound; and
   d) adhering a fourth layer over said third absorbent layer for allowing limited flow of exudates from a wound site to the third absorbent layer, as well as transference of either said hemostatic agent and said antimicrobial agent to a wound.

11. A method of producing an adhesive bandage for treating acute wounds, burn wounds and irritations consisting of the steps of:
   a) providing an adhesive bandage which includes
      a first base layer for covering the wound site and an area round the wound site;
   b) coating an adhesive layer over said first layer, for adhering the adhesive bandage to a wound site;
   c) adhering a third absorbent layer over said second layer, for absorbing exudates from a wound site; and
   d) adhering a fourth layer over said third absorbent layer, said fourth layer including either a hemostatic agent, antimicrobial agent or both, selected from the group consisting of chitosan niacinamide ascorbate salt, niacinamide ascorbate, and combinations thereof, for transferring to a wound; and wherein said fourth layer allows limited flow of exudates from a wound site to the third absorbent layer, as well as transference of said hemostatic agent and said antimicrobial agent to a wound.

12. A method of treating a acute wounds, burn wounds and irritations comprising the steps of: contacting an acute wound, burn wound and irritation with an adhesive bandage comprising:
   a first layer for covering the wound site and an area around the wound site, said first layer including a top surface and bottom surface;
   a second adhesive layer over said first layer bottom surface, for adhering the adhesive bandage to a wound site;
   a third absorbent layer over said second layer, for absorbing exudates from the wound site;
   a fourth layer over said third absorbent layer for allowing limited flow of exudates from the wound site to the third layer; and
   at least one of an antimicrobial agent and a hemostatic agent selected from the group consisting of chitosan niacinamide ascorbate salt, niacinamide ascorbate, and combinations thereof, each associated with said adhesive bandage in a position where said agent will come in contact with the wound site, and which are transferable from the adhesive bandage to the wound site.

* * * * *